(12) United States Patent
Jabobs et al.

(10) Patent No.: US 6,484,556 B1
(45) Date of Patent: Nov. 26, 2002

(54) THIN FILM DETECTION DURING FLUID ASPIRATION

(75) Inventors: Merrit Jabobs, Fairport, NY (US); Michael Avdenko, Rochester, NY (US); Christopher Michael Parobek, Honeoye Falls, NY (US); Jim Shaw, Hilton, NY (US)

(73) Assignee: Ortho Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 09/711,483

(22) Filed: Nov. 13, 2000

(51) Int. Cl.[7] .............................. G01F 19/00; G01N 1/14; G01N 35/02
(52) U.S. Cl. .................... 73/1.74; 73/864.18; 702/47; 702/55; 436/51; 436/54
(58) Field of Search .............................. 73/1.74, 864.15, 73/864.16, 864.17, 864.18, 864.01, 53.01; 436/50, 51, 54; 702/47, 50, 55

(56) References Cited

U.S. PATENT DOCUMENTS

| | | | |
|---|---|---|---|
| 4,794,085 A | | 12/1988 | Jessop et al. ................. 436/54 |
| 5,143,849 A | * | 9/1992 | Barry et al. ................. 422/100 |
| 5,452,619 A | * | 9/1995 | Kawanabe et al. ............ 73/863 |
| 5,488,854 A | * | 2/1996 | Kawanabe et al. ......... 73/19.05 |
| 5,499,545 A | * | 3/1996 | Kimura et al. ................. 222/55 |
| 5,537,880 A | * | 7/1996 | Takeda et al. .................. 73/40 |
| 5,540,081 A | * | 7/1996 | Takeda et al. .............. 340/626 |
| 5,723,795 A | * | 3/1998 | Merriam ......................... 137/1 |
| 5,750,881 A | * | 5/1998 | Dorenkott et al. ........... 422/160 |
| 5,814,275 A | * | 9/1998 | Lewis et al. ................. 422/100 |
| 6,060,320 A | | 5/2000 | Dorenkott et al. ............. 436/54 |
| 6,094,966 A | * | 8/2000 | Papen et al. ................. 73/1.74 |
| 6,119,533 A | * | 9/2000 | Gherson et al. ............... 702/32 |
| 6,121,049 A | | 9/2000 | Dorenkott et al. ............. 436/50 |
| 6,158,269 A | * | 12/2000 | Dorenkott et al. ........... 422/100 |

FOREIGN PATENT DOCUMENTS

EP      0 215 534      3/1987

* cited by examiner

Primary Examiner—Hezron Williams
Assistant Examiner—Michael Cygan

(57) ABSTRACT

The accurate determination of the presence of a fluid in a container is determined by assessing the difference in various pressure readings relative to a threshold value. The method distinguishes between actual aspiration of a fluid and aspiration of a film that can otherwise lead one to believe that fluid has been aspirated when it has not. The method is particularly useful in clinical analyzers such as automated enzyme immunoassay devices.

3 Claims, 3 Drawing Sheets

THIN FILM DETECTION DURING FLUID ASPIRATION

BACKGROUND

This invention relates to the to the automated transport of fluids.

Fluid dispensers are integral components of most automated clinical analyzers. U.S. Pat. No. 4,794,085 to Jessop proposes an apparatus and method for detecting sample aspiration in such instruments. The device and method employ a pressure sensor to detect the presence of the fluid meniscus in the sample container. When the meniscus is sensed it is assumed that fluid lies beneath and can then be aspirated and dispensed. This method and device have proven useful. However, fluids that are to be aspirated do not always present a meniscus that can reliably be used to determine the location of the surface of the fluid. When this happens, such analyzers can indicate that sufficient fluids have been aspirated when such is not the case. Accordingly, a method for indicating when such a false reading has occurred would be useful.

SUMMARY OF THE INVENTION

The invention is a method for determining whether a fluid has been aspirated. In the method, pressure readings are taken during a slow aspirate process and during a priming process. Reference pressure measurement also occurs after priming. Two differences are determined, one is the difference between pressure readings during slow aspirate and the reference pressure and the other is the difference between the reference pressure and pressure readings during prime. If either is less than a predetermined threshold then an error message is communicated.

In a further embodiment of the invention, the pressure reading during slow aspirate is a trough reading and the pressure reading prime is a prime reading where trough and peak values may be statistical (e.g. numerically averaged values) at or near the trough and peak readings.

In yet a further embodiment of the invention, the threshold is determined statistically. In this embodiment, a parameter such as CpK can be used to calculate the effectiveness that the film of fluid will be detected without a high frequency of false positive.

DESCRIPTION OF THE PREFERRED EMBODIMENTS

The invention is useful in any dispensing apparatus or method in which a fluid is aspirated into a delivery vessel such as a sample probe in a clinical analyzer.

Terms such as "up", "down", "lower", "vertical", "horizontal", and "bottom", as used herein refer to the orientation of parts when the apparatus is positioned in its customary position of use.

Figure 1:
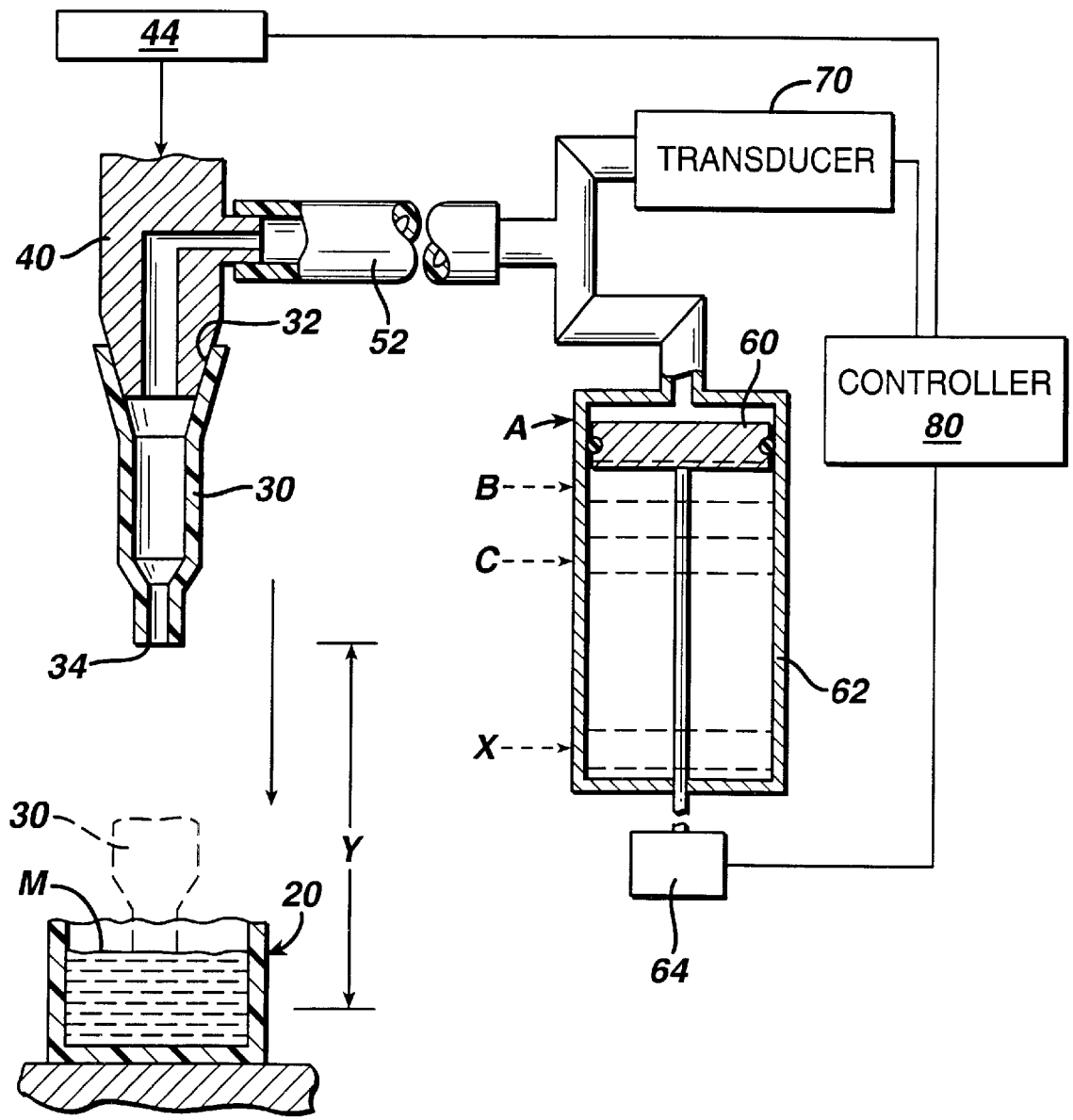
FIG. 1 is a fragmentary perspective view of a dispensing apparatus with which the method of the invention can be practiced.

A portion of a preferred dispensing apparatus is illustrated in FIG. 1. A plurality of sample containers 20 is provided in a tray (not shown), which also supports removable, disposable dispensing containers 30. The containers 30 have a larger aperture 32 at one end to mate with the probe thus forming the tip of the probe when mated. They also have a smaller aperture 34 at the opposite end for aspirating and dispensing. A probe 40 is mounted for vertical and horizontal movement on a frame (not shown), such movement being provided respectively by a motor 44 and gear (not shown), and by a car (not shown) carrying the probe 40 horizontally on rails (not shown). The combined movement of the car and probe is effective to carry the probe vertically within the plane of the paper in FIG. 1.

A pressure line 52 provides a partial vacuum or a partial pressure, relative to atmospheric pressure, to a dispensing container 30 picked up by the probe. The pressure or vacuum is provided by means such as a piston as described in U.S. Pat. No. 4,794,085, incorporated by reference herein. A pressure transducer as described in the '085 patent is used to sense the pressure in container 30, for example to determine when p proper dispensing of the fluid out of container 30 occurs.

An appropriate controller 80 is provided to coordinate the actuation of the motors that drive the pistons 60 or other devices that adjust pressure in the probe in response to conditions sensed by the transducer. The controller generally comprises a microprocessor and is connected to the piston through connector 64. Pistons 60 are contained in piston housing 62.

The described apparatus is used as follows to detect the penetration of the fluid meniscus M, by the aperture 34 of container 30:

a) assume the total distance from aperture 34 to a point that will always penetrate the fluid (the minimum fill) is initially dimension Y, b) while container 30 is still at atmospheric pressure, a base pressure value is established; this is done by generating a signal by the pressure transducer 70 before aspiration of fluid is begun, c) container 30, positioned on the end of probe 40, is lowered to position Y (and then lower as indicated in d) below, if necessary); throughout this process, signals are again produced by transducer 70, and those signals are compared to the base pressure signal previously generated; if there is no difference greater than a predetermined amount, then the fluid meniscus M still has not been penetrated, d) if the fluid meniscus has not been penetrated, step c) is repeated until either a transducer signal is generated at a new level that exceeds the predetermined value, thus indicating the penetration of meniscus, or the advancement of the probe would exceed a safety factor (a level beyond which the container 30 may crash into the container 20); if the safety factor is exceeded or the pressure differences do not exceed the predetermined amount, fluid aspiration is not conducted for that sample and an error message is generated.

When the transducer signal indicates fluid penetration, aspiration of fluid in container 30 is conducted by lowering the probe 40 so that container 30 is in fluid contact with fluid in container 20. A negative pressure is then induced via pressure line 52, drawing fluid into container 30 in the 30 manner known in the art. Probe 40 descends as needed to keep pace with the falling meniscus level. The process thus far described is referred to as "fast aspirate" and, as is indicated by its moniker, can be conducted as rapidly as the mechanics of the system will permit. In the typical fast aspirate step used in the preferred automated enzyme immunoassay analyzer, about 30 µl of sample is aspirated into container 30. This volume is the combination of "dead volume in the tip" and the prime volume and is the same for all dispensed volumes in the examples of this application. Of course, the recitation of this volume in no way limits the scope of the invention and is merely provided for exemplary purposes.

Throughout fast aspirate signals are again produced by transducer 70 and each such signal is compared to another base pressure reading. The process is interrupted and an error message is generated if the signal is less than a predetermined value empirically determined to indicate that insufficient fluid has been aspirated. Such an event would occur, for example, when a bubble that would interfere with the subsequent use of the fluid has been aspirated.

Following the fast aspirate step, all of the previous steps that ensure that meniscus penetration and fluid aspiration are appropriate are again conducted and another predetermined volume of fluid is aspirated into container 30. This process is referred to as "slow aspirate". In the typical slow aspirate step used in the preferred automated enzyme immunoassay analyzer, about 10 µl of sample is aspirated back into container 30 (this volume is equivalent to the volume to be dispensed). As noted above, the recitation of this volume in no way limits the scope of the invention and is merely provided for exemplary purposes.

Since the slow aspirate process is conducted by the induction of a negative pressure, a convex meniscus is formed in the upper portion of container 30. This is undesirable and is ameliorated by reducing the negative pressure used to contain the fluid in container 30 so that a small predetermined amount of fluid is expelled back into container 20. This process is referred to as "priming". In the typical priming step used in the preferred automated enzyme immunoassay analyzer, about 10 µl of sample is primed back into container 20. Here too, the recitation of this volume in no way limits the scope of the invention and is merely provided for exemplary purposes.

The process thus far described is well known in the art and is commonly used in commercial clinical analyzers such as automated enzyme immunoassay analyzers. In such applications aspirated fluid is subsequently dispensed in reaction vessels for further combination with, for example, other reagents, in such applications.

During the previously described process it sometimes happens that a thin film of fluid is formed in container 30 above the meniscus of the fluid that is to be aspirated. The formation of such a film can be problematic. That is, the pressure sensing methods described can detect the film and determine that it has a different response to pressure than does air. This can lead to a result that indicates that a sufficient volume of fluid has been aspirated even when it has not. It is important to differentiate between a thin film of fluid above the primary volume of fluid and bubbles or foam above the fluid. Each produces a different pressure signature and needs to be detected differently. Employment of the following method avoids this outcome.

Pressure readings are taken during the slow aspirate phase. Preferably, a number of such readings are taken from which a statistically representative value is determined. This value is determined at or near the trough of the slow aspirate signal. This value is referred to as level B. Similarly, a number of pressure readings are taken during the prime phase from which a statistically relevant value is determined. This value is determined at or near the peak of the prime signal and is referred to as level A. A reference pressure value is also determined. This value is referred to as level C.

Figure 3:
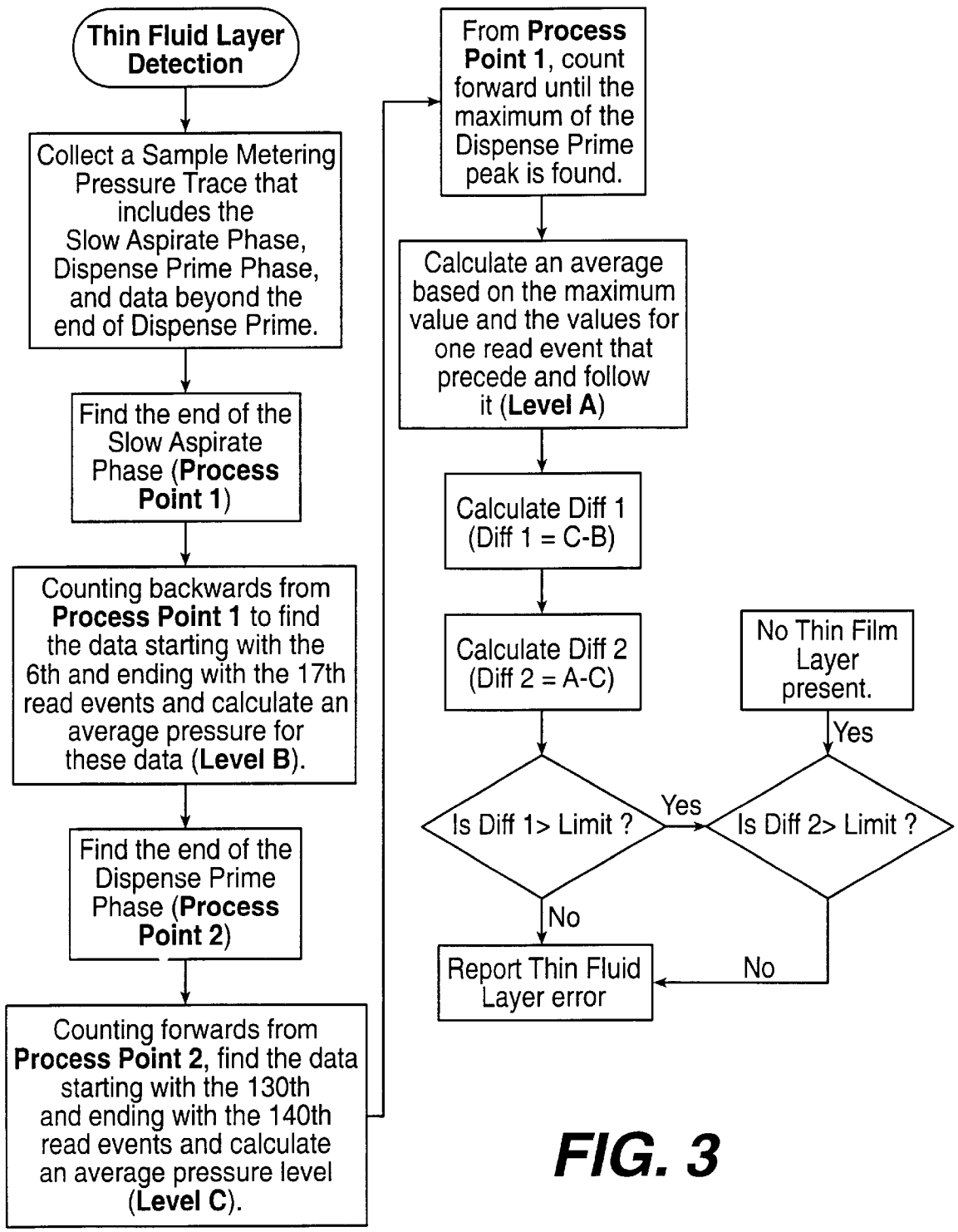
FIG. 3 is a flow chart for programming the controller of the described apparatus to carry out the invention.

Two different difference values are then determined. Difference value 1 (Diff 1) is calculated by subtracting level B from level C. Difference value 2 (Diff 2) is calculated by subtracting level C from level A. If either Diff 1 or Diff 2 is less than a predetermined threshold then container 30 contains a thin film that can obscure the accurate measure of the volume aspirated. In such a case, the remainder of the aspirated fluid in container 30 is discarded and a message is generated indicating that such events have occurred. The sample can be dispensed into a vessel that would have undergone subsequent processing such as mixture with reagents but no such subsequent processing need be conducted. This process is also shown graphically in the flow chart of FIG. 3.

The reference value is preferably determined by taking a large number of pressure readings after the end of priming (preferably, the time at which the pump stops during the prime cycle). Preferably, more than 50 such readings are taken, more preferably, more than 100 readings are taken, and most preferably 130–140 readings are taken. An arithmetic average of these readings is then used as the reference value. Alternative methods for establishing the reference value include using the minimum pressure reading taken over the course of a number of readings or by integrating a plot of pressure readings taken over time during some step in the process other than slow aspirate or prime steps. The reference value may also be obtained via moving average or by a combination of moving average and any of the aforementioned methods.

Level A is preferably determined as follows. A number of pressure readings (preferably 5 to 20, more preferably 6 to 17, and most preferably 10 to 17 readings) are taken during the slow aspirate cycle. The end of the cycle occurs when the pump stops during the slow aspirate step. An arithmetic average of these readings is then Level A. Alternative methods for determining level A include using the minimum pressure reading taken over the course of a number of readings or by integrating a plot of pressure readings taken over time during the slow aspirate step. Level A may also be obtained via moving average or by a combination of moving average and any of the aforementioned methods.

Level B is preferably determined as follows. The peak pressure during the prime step is determined. Preferably at least two additional readings are taken, one just prior to the peak pressure and another just after the peak pressure are also taken. The arithmetic average of these readings is then Level B. Preferably, the readings just before and just after the peak pressure readings are taken at intervals of about 500–750 milliseconds before/after the peak pressure readings. Alternative methods for determining Level B include using the maximum pressure th reading taken over the course of a number of readings or by integrating a plot of pressure readings taken over time during the prime step. Level B may also be obtained via moving average or by a combination of moving average and any of the aforementioned methods.

The threshold value to which Diff 1 and Diff 2 are compared is determined as follows. True positive (sample volume accurately measured for sample that is present) and true negative distributions (the absence of sample volume accurately measured as absent) are constructed from pressure traces using direct observations (multiple pressure readings during the relevant cycles). Arithmetic mean and standard deviation values for each distribution are determined.

To account for differences in atmospheric pressure from place to place (i.e., due to differences in altitude), distributions for true positive and true negative events can be shifted by a constant factor determined empirically under different pressure conditions. This can be determined by use of the following well-known relationship:

$$\frac{\Delta P_2}{\Delta P_0} = \exp\left(\frac{Mgz}{RT}\right)$$

Where:
- $\Delta P_2$=Pressure at new altitude (atm)
- $\Delta P_0$=Pressure at reference altitude (atm)
- M=Molecular Weight of the gas (g/mole)
- g=980.665 cm/sec2
- z=Altitude change (cm)
- R=8.3144×10$^7$ (ergs/deg mole)
- T=Temperature (degrees K).

Upper and lower pressure limits can be then be established using the mean and standard deviation determinations. In the preferred method, a Process Capability Index (CpK) value is used to adequately protect against both false negatives and false positives. This index represents the ability of the detection algorithm to discriminate between anomalous and non-anomalous events on a short-term basis. It is a tool for considering the spread and mean shift of a process that should be confined between upper and lower limits in processes exhibiting a normal distribution of the spread of data. CpK values are determined according to methods well known in the art. It is preferred that the Cpk is determined according to the following relationship:

$$Cpk=\min\ [(USL-\mu)/3\sigma,\ (\mu-LSL)/3\sigma]$$

where:
- USL is the upper specification limit
- LSL is the lower specification limit
- $\mu$ is the mean of the data
- $\sigma$ is the standard deviation of the data The threshold values are determined by solving for USL and LSL when an acceptable Cpk value is assigned. The larger the CpK, the lesser is the chance of a false positive. In the case of automated enzyme immunoassays, a CpK of 2 or more guards against false negatives and is preferred. A CpK of more than 1 is sufficient to guard against false positives. This assures that there will be no more than three false negative detections out of one million occurrences of a formation of a thin film of fluid. It also assures that there will be fewer than one false positive detections out of 100 sample containers tested.

Figure 2:
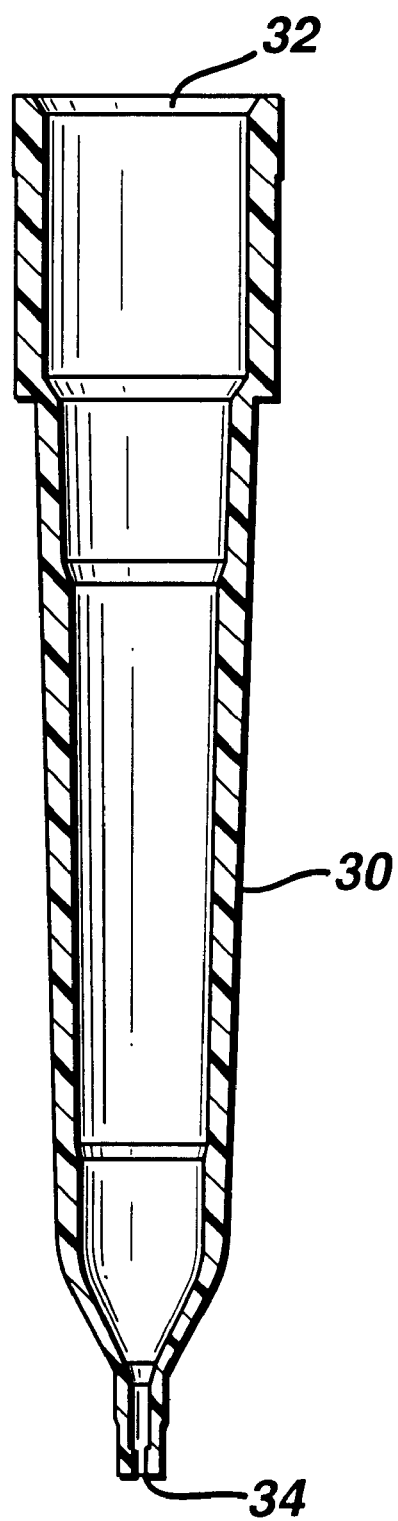
FIG. 2 is a perspective view of fluid containers that are useful in the practice of the invention.

In the most preferred embodiment of this invention, container 30 is made from injection moldable thermoplastic such as polypropylene and has the geometry shown in FIG. 2. Fluid carrying portion 30 is about 30 mm in length (measured according to dimension 30d) with an outside diameter ranging from 1.5 mm at its narrowest to 6.8 mm at its widest. Smallest aperture 34 has a diameter of about 0.5 mm with a cylindrical portion 32 that is about 3 mm in length. When using such containers, the process for determining threshold values described above yields a threshold value of 0.01 to 2 kPa. Preferably, the cutoff is set at about 0.065 kPa. Establishing threshold values when using containers of other geometries and dimensions is readily accomplished with routine experimentation according the method described above.

EXAMPLES

Testing was done on four ECi automated enzyme immunoassay analyzers commercially available from Ortho Clinical Diagnostics, Rochester, N.Y. Containers for aspirating fluid were the type commercially sold as disposables for use with the analyzers and conform to the preferred embodiment described above.

Four different fluid volumes were aspirated during slow aspirate: 10, 20, 25 and 80 $\mu$l with an attempt at creating four thin film bubbles at each volume on each analyzer using 4 centipoise and normal serum as the fluid in the tubes. This test was done using 13 mm glass primary collection tubes. Testing was also done using water in a 2 ml cup with the cup support set to the lowest tolerance to simulate worst-case tip immersion. This was done to create a condition simulating very low pressure signal for slow aspirate and prime without a thin film of fluid present in the tube or cup.

Across the four analyzers tested there were 88 thin film events observed. All of the thin film events were detected with the new method (with the threshold set to 0.065 kPa). None of the "non-thin film" aspirates (n=229) were falsely flagged as an error.

The robustness of the process was tested by conducting the same process by aspirating and priming low viscosity fluid (water). This analysis was done a second time with eight high pressure outliers removed from the data set. These values inflate the standard deviation but did not increase the likelihood that a false error code occurred.

No false positive or negative results were produced across the fluid types and four analyzers tested.

The thin film fluid detection (based on this data when the thin film bubble was present) was also shown to be independent of fluid type and aspirate volume.

We claim:
1. A method for determining whether a fluid has been properly aspirated into a fluid container comprising:
   a) determining the pressure inside the gas filled container during initial aspiration of the fluid;
   b) determining the pressure inside the container while dispensing a portion of the fluid;
   c) determining the pressure inside the container at some time other than during step a) to establish a reference pressure;
   d) determining the difference between the value attained in step a) and the reference pressure;
   e) determining the difference between the reference pressure and the value attained in step b); and
   g) indicating that a thin film of fluid has been aspirated if the absolute values obtained in step d) or step e) are less than a predetermined threshold wherein the threshold is determined statistically as the CpK that is acceptable for a given false positive and/or false negative rate.
2. The method of claim 1 wherein the threshold value is 0.01 to 2 kPa.
3. The method of claim 2 wherein the threshold value is about 0.065 kPa.

* * * * *